United States Patent [19]

Torossian et al.

[11] 4,427,671
[45] Jan. 24, 1984

[54] STEROIDS ESTERIFIED IN POSITION 17 AND THIOESTERIFIED IN POSITION 21, A PROCESS FOR PREPARING THEM AND THEIR USE AS MEDICAMENTS

[75] Inventors: Diéran R. Torossian, Bourg-la-Reine; Gilbert G. Aubard, Palaiseau; Claude P. Roux, Paris; Agnès G. Grouhel, Meudon, all of France

[73] Assignee: S.I.P.S.Y., Avrille, France

[21] Appl. No.: 397,715

[22] Filed: Jul. 13, 1982

[30] Foreign Application Priority Data

Jul. 30, 1981 [FR] France ................................ 81 14860

[51] Int. Cl.³ .......................... A61K 31/56; C07J 7/00
[52] U.S. Cl. ................................. 424/243; 260/397.45
[58] Field of Search ..................... 260/397.45; 424/243

[56] References Cited

U.S. PATENT DOCUMENTS

| | | | |
|---|---|---|---|
| 3,312,591 | 4/1967 | Elks et al. | 260/397.45 |
| 4,243,664 | 1/1981 | Annen et al. | 260/397.45 |
| 4,269,778 | 5/1981 | Torossian et al. | 260/397.45 |
| 4,343,739 | 8/1982 | Villax et al. | 260/397.45 |
| 4,361,558 | 11/1982 | Wieland | 260/397.45 |

FOREIGN PATENT DOCUMENTS

| | | | |
|---|---|---|---|
| 2070077 | 9/1971 | France | 260/397.45 |
| 2081395 | 12/1971 | France | 260/397.45 |
| 2231374 | 12/1974 | France | 260/397.45 |
| 2442856 | 6/1980 | France | 260/397.45 |

*Primary Examiner*—Elbert L. Roberts
*Attorney, Agent, or Firm*—Cushman, Darby & Cushman

[57] ABSTRACT

Compounds of formula:

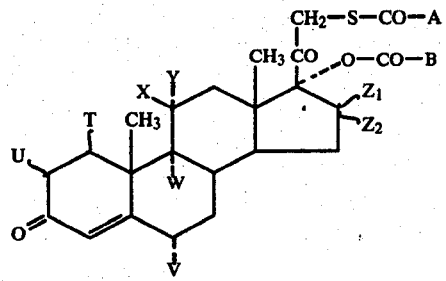

wherein A and B each represent, independently of each other, a straight-chained or branched alkyl group having from 1 to 6 carbon atoms or a phenyl group optionally mono- or polysubstituted by alkyl radicals having from 1 to 6 carbon atoms, alkoxy groups having from 1 to 6 carbon atoms or halogen, T and U, independently of each other, represent hydrogen atoms or together form a double bond, V is a hydrogen atom or a methyl group at the α-position, W is a hydrogen atom or a halogen atom at the α-position, X is a hydroxy group at the β-position and Y is a hydrogen atom or X and Y may together represent an oxygen atom, and $Z_1$ is a hydrogen atom, a methyl group at the α- or β-position, while $Z_2$ is a hydrogen atom, or $Z_1$ and $Z_2$ together form a methylene group. These compounds have anti-inflammatory activity.

24 Claims, No Drawings

STEROIDS ESTERIFIED IN POSITION 17 AND THIOESTERIFIED IN POSITION 21, A PROCESS FOR PREPARING THEM AND THEIR USE AS MEDICAMENTS

The invention relates to new steroids, a process for preparing them and their use in medicine.

One of the main steroids used as a local anti-inflammatory agent is betamethasone 17,21-dipropionate. It is found that, in conventional pharmacological tests, the majority of the products according to this invention are more active and, in some cases, more than 100 times more active than the above-mentioned anti-inflammatory agent.

The compounds according to the invention correspond to the formula:

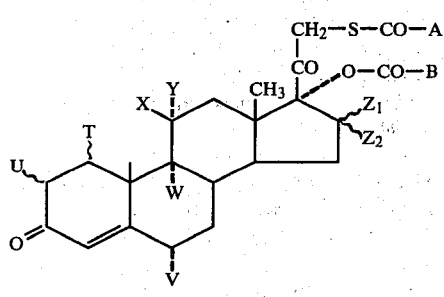

wherein A and B each represent, independently of each other a straight-chained or branched alkyl group having from 1 to 6 carbon atoms or a phenyl group optionally mono- or polysubstituted by alkyl radicals having from 1 to 6 carbon atoms, alkoxy groups having from 1 to 6 carbon atoms or halogen, T and U, independently of each other, represent hydrogen atoms or together form a double bond, V is a hydrogen atom or a methyl group at the α-position, W is a hydrogen atom or a halogen atom at the α-position, X is a hydroxy group at the β-position and Y is a hydrogen atom or X and Y may together represent an oxygen atom, and $Z_1$ is a hydrogen atom, a methyl group at the α- or β-beta position, whilst $Z_2$ is a hydrogen atom, or $Z_1$ and $Z_2$ together form a methylene group.

These compounds differ from those described in French Pat. No. 2,081,395 in that they are not fluorinated at the 6 position. Although French Pat. No. 2,081,395 does not give any numerical data as to the activity of the compounds which it claims, these compounds, which have not replaced betamethasone 17,21-dipropionate on the market, can only be less effective than this latter compound.

In French Pat. No. 2,070,077 a process for preparing dicarbonyl compounds is described. It is proposed that a sulphide be reacted with bases. The sulphur starting substances mentioned include, last of all (page 4), those corresponding to a formula (I). These starting compounds are not presented as having any pharmacological properties. Even today, these starting substances are unknown in the literature. The French Patent does not give any information or describe any physical characteristics whatsoever relating to these compounds. The patent does not describe any process for preparing these compounds, which are still unknown today.

The compounds which are closest to those of formula I and are described in French Pat. No. 2,070,077 are monothioesters at the 21 position. It would have been logical to prepare the 17-esters, 21-thioesters by esterifying the monothioesters. In fact, it has been found that this method of synthesis does not work. The reaction does not occur. It is therefore clear that formula (I) is simply a theoretical conjecture which does not correspond to any practical embodiment and that it was merely drawn up on paper without a single compound corresponding to this formula being prepared and without any method of synthesis, however difficult, being proposed. This does not constitute a description of the compounds under the terms of the law relating to patents but simply refers to these compounds by the expedient of an abstract formula.

The products of the invention are prepared by reacting a steroid 21-sulphonate of formula

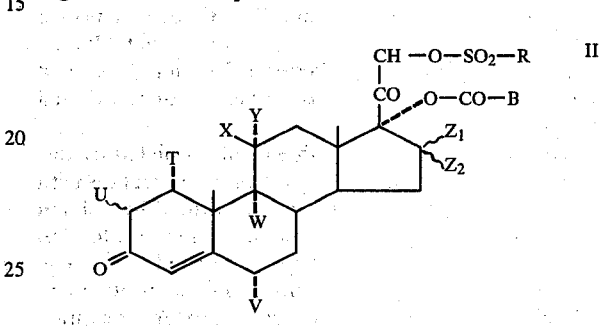

wherein R corresponds to a lower alkyl radical ($C_1$ to $C_{12}$, particularly $C_1$ to $C_4$), with an alkali metal thiocarboxylate of formula:

$$M-S-CO-A \qquad III$$

wherein M represents an alkali metal atom.

21-Sulphonates are known per se and their preparation by various methods has already been described.

The method generally used consists in taking a 17α,21-dihydroxy steroid as starting material and:

(1) esterifying the 17α-hydroxy structure, which is effected by a well-known method, using a suitable tri(lower alkyl)orthocarboxylate in an inert organic solvent such as dimethyl sulphoxide or dimethyl formamide and in the presence of an acid catalyst such as p-toluene sulphonic acid.

The 17,21-orthoester formed is selectively hydrolysed at 21 by means of a moderately strong acid such as acetic acid in order to obtain the 17α-ester-21-hydroxy derivative.

(2) Preparing the sulphonic ester at the 21-position of the above-mentioned derivative; this is effected by processes which are known per se, for example by the action of an alkyl sulphochloride in pyridine.

The products of the invention are prepared by reacting the 21-sulphonate of formula (II) with the alkali metal thiocarboxylate of formula (III) in an aprotic solvent under suitable conditions. The crude product obtained is generally purified by column chromatography, then by recrystallisation from an alcohol, notably an alkanol of low molecular weight, to obtain a sufficiently pure product.

In a first stage, the alkali metal thiocarboxylate is prepared by salifying an S-thiocarboxylic acid with an alkali metal alkoxide in an aprotic solvent such as a ketone or an amide.

This reaction is effected by adding a stoichiometric quantity or a quantity up to 20% less than stoichiometric of an approximately 4 N methanolic solution of sodium methoxide to a solution of 10 to 50% by weight of S-thiocarboxylic acid in acetone or in hexamethylphosphorotriamide (hereinafter referred to as H.M.P.T.). The mixture is stirred for a period of from 10 minutes to 3 hours, but preferably for a period of from 15 to 45 minutes.

The 21-sulphonate of formula (II), in solution in the same solvent as hereinbefore, is added to the above mixture. This product is used in a stoichiometric deficiency relative to the S-thiocarboxylic acid. From 0.2 to 0.9 mole of compound (II), preferably from 0.5 to 0.85 mole, are used relative to 1 mole of acid.

Depending on the solvent used and the reagents in question, the reaction is then carried out at a temperature of between about 0° and 100° C. over a period which varies from 5 minutes to hours. Preferably, the reaction temperatures are between 20° and 60° C. and the duration of the reaction is between 10 minutes and 8 hours.

The product formed is subsequently isolated by different methods involving distillation or extraction with solvents. The product is generally purified by column chromatography followed by final recrystallisation from an alcohol or a mixture of alcohol and water. The preferred alcohols are methanol and ethanol, whilst of the mixtures of alcohol and water the mixture consisting of 80% methanol and 20% water is preferred.

Finally, the invention relates to a medicament incorporating as active ingredient a compound according to the invention.

The following Examples illustrate the invention. In these Examples:

(a) The degree of purity of the products obtained was monitored by thin layer chromatography:
support: silica gel 60 F 254 (supplied by Merck),
deposits: 100 mcg of product,
disclosure: observation of plates under ultra-violet light with a wavelength of 254 nm.

(b) The melting points were determined using a "Mettler FPl" apparatus and have not been corrected.

(c) Elementary analysis of the products was carried out; the results of this analysis are not given in the Examples. They agree closely with the theoretical results. The same applies to the infrared absorption spectra, which were recorded using the method of the lozenge suspended in KBr. The main absorptions, compatible with the structures described, are not given.

(d) The nuclear magnetic resonance spectra of the proton are given. These spectra were recorded in solution in deuterochloroform $CDCl_3$ on a 60 MHz apparatus.

The chemical displacements are given in p.p.m. relative to the tetramethylsilane taken as a reference.

The appearance of the signals and their presumed positions on the structure are given:
s = singlet
d = doublet
t = triplet
q = quadruplet
m = mass
J = coupling constants in $H_z$
Example: 0.98 (s—18 $CH_3$) is the singlet signal corresponding to the three hydrogens carried by the carbon 18.

Note: "Florisil" is the brand name of a support for chromatography (Floridin Company, U.S.A.).

EXAMPLE 1

11β-hydroxy-pregn-4-ene-3,20-dione (or hydrocortisone) 17-valerate, 21-thiovalerate A and B=normal butyl T, U, V, W, Y, Z=H, X=OH.

28.3 grams (0.24 mol) of S-thiovaleric acid and 900 ml of acetone are placed in a reactor.

67 ml of a 3.58 N methanolic solution of sodium methoxide (0.24 mol) are added, with stirring, at a temperature at about 20° C.

After 1 hour's stirring at ambient temperature, 90.0 grams (0.17 mol) of cortisol 17-valerate, 21-mesylate in solution in 1800 ml of acetone are added.

The suspension obtained is heated to the reflux temperature of the acetone (56.2° C.) and maintained at this temperature, with stirring, for 4 hours.

The acetone is eliminated by distillation until a residual volume of about 1 liter is obtained.

The residue is precipitated in two liters of cold water; the gum which forms is extracted with diethylether.

The combined etheric phases are evaporated. Weight of residue: 94 grams.

The residue is purified by column chromatography using 3.6 kg of "Florisil" (60- particle size less than 0.15 mm). By eluting first with a mixture of benzene and acetone (98:2 v/v), then with a mixture of benzene and acetone (95:5 v/v), 42.5 grams of purified product can be recovered using the latter solvent.

This product is finally recrystallized from 1200 ml of a mixture of methanol and water (8:2 v/v).
Weight = 16.6 grams
Yield = 17.7%
Melting point = 131° C.
NMR = 0.93 (t, $CH_3$ esters); 0.98 (s, 18 $CH_3$); 1.45 (s, 19 $CH_3$); 1.75 (m, 11 βOH); 2.35 (q, $CH_2$ esters); 3.80 (s, 21 $CH_2$); 4.5 (M, 11 CH); 5.70 (s, 4 CH).

EXAMPLE 2

11β-hydroxy-pregn-4-ene-3,20-dione (or hydrocortisone) 17-valerate, 21-thiopivalate A = tert.butyl; B = n-butyl; T, U, V, W, Y, Z=H; X=OH.

Using the same method as in Example 1, starting from 60.0 grams (0.114 mol) of cortisol 17-valerate, 21-mesylate, 19.0 grams (0.160 mol) of S-thiopivalic acid and 45.6 ml (0.160 mol) of a 3.5 N methanolic solution of sodium methoxide, a product is obtained which is finally purified by recrystallisation from a mixture of methanol and water (80:20 v/v).
Weight = 18.0 grams
Yield = 28.8%.
Melting point = 206° C.
N.M.R. = 0.92 (t, $CH_3$ esters); 0.96 (s, 18 $CH_3$); 1.27 (s, t-butyl); 1,45 (s, 19 $CH_3$); 1.70 (m, 11 β—OH; 2.01 (q, $CH_2$ ester); 3.79 (s, 21 $CH_2$); 4.50 (m, 11 CH); 5.70 (s, 4 CH).

EXAMPLE 3

Pregna-1,4-diene-3,11,20-trione (or prednisone) 17-butyrate, 21-thioacetate.

A = methyl; B = n-propyl; T and U=O (double bond); V, W, Z=H; X and Y=keto function.

290 ml of hexamethylphosphorotriamide (H.M.P.T.) and 8.7 grams of S-thioacetic acid (0.115 mole) are placed in a 1 liter reactor. 25.2 ml of a 4.5 N methanolic solution of sodium methoxide (0.115 mole) are added.

The mixture is stirred for 30 minutes at ambient temperature, then 29.1 grams (0.0574 mole) of prednisone 17-butyrate, 21-mesylate in solution in 580 ml of H.M.P.T. are added thereto.

After 10 minutes' stirring at ambient temperature, the reaction mixture is precipitated in ice-cold water and the mixture is extracted with diethyl ether.

The residue of etheric phases represents 26.0 grams of a mixture of products which is purified by chromatography on a column of 500 grams of "Florisil".

By eluting with a mixture of hexane and acetone 13.7 grams of product are obtained which are finally purified by recrystallisation from a mixture of methanol and water (80:20 v/v).

Weight=9.6 grams.
Yield=34.4%.
Melting point=114.5° C.
N.M.R.=0.72 (s, 18 $CH_3$); 0.98 (t, $CH_3$ ester at 17); 1.45 (s, 19-$CH_3$); 2.35 (t, $CH_2$ ester); 2.37 (s, ester at 21); 3.80 (s, 21-$CH_2$); 6.19 (s, 4-CH); 6.37 (d, J=2 Hz, 2-CH); 7.75 (d, J=10 Hz, 1-CH).

EXAMPLE 4

11$\beta$-hydroxy-6$\alpha$-methyl-pregna-1,4-diene-3,20-dione (or 6$\beta$-methylprednisolone) 17-benzoate, 21-thioacetate.

A=methyl; B=phenyl:T and U=O (double bond); V=methyl at the $\alpha$ position; W, Y and Z=H; X=OH.

Using an electromagnetic stirrer, a solution of 1.765 ml of S-thioacetic acid (24.8 mmol) in 165 ml of HMPT is prepared.

Then 5.865 ml of a 4 N methanolic solution of sodium methoxide (23.5 mmol) are added.

After 1 hour's stirring 8.2 grams (15.6 mmol) of 6$\alpha$-methyl-prednisolone 17-benzoate, 21-methylate are added.

The reaction mixture is then stirred for 6 hours at ambient temperature and then pecipitated in water.

The mixture is extracted with diethylether. The residue of the etheric phase is purified by chromography on a column of 300 grams of "Florisil".

4.5 grams of purified product are obtained which is finally recrystallized from methanol.

Weight=3.1 grams.
Yield=37.0%.
Melting point=215° C. (decomposition).
N.M.R.=1.05 (s, 18, $CH_3$); 1.15 (d, 6-$CH_3$); 1.52 (s, 19-$CH_3$); 1.95 (m, 11$\beta$ OH); 2.35 (s, $CH_3$ ester at 21); 4.60 (m, 11-CH); 7.65 (m-phenyl nucleus).

The following products are obtained using the same procedure as in Example 4 with the suitable reagents:

EXAMPLE 5

11$\beta$-hydroxy-6$\alpha$-methyl-pregna-1,4-diene-3,20-dione (or 6$\alpha$-methylprednisolone) 17-propionate, 21-thiopropionate.

A and B=ethyl; T and U=O (double bond); V=methyl at the $\alpha$ position; W,Y and Z=H; X=OH
Yield=11%
Melting point=161° C.
N.M.R.=1.00 (s, 18-$CH_3$); 1.10 (d, 6-$CH_3$)=1.20 (s, 19-$CH_3$) 1,47 (s, propionic esters); 1.68 (m, 11$\beta$—OH); 3.85 (s, 21-$CH_2$); 6.08 (s, 4-CH)

EXAMPLE 6

11$\beta$-hydroxy-6$\alpha$-methyl-pregna-1,4-diene-3,20-dione (or 6$\alpha$-methylprednisolone) 17-valerate, 21-thiovalerate.

A and B=butyl; T and U=O (double bond); V=methyl at the $\alpha$ position; W, Y and Z=H; X=OH
Yield=47.4%
Melting point=170° C.
N.M.R.: 0.98 (s, 18-$CH_3$); 1.15 (d, 6-$CH_3$)=1.47 (s, 19-$CH_3$) 1,95 (m, 11$\beta$-OH); 3.80 (s, 21-$CH_2$); 6.07 (s, 4-CH)

EXAMPLE 7

11$\beta$-hydroxy-6$\alpha$-methyl-pregna-1,4-diene-3,20-dione (or 6$\alpha$-methylprednisolone) 17-valerate, 21-thioacetate.

A=methyl; B=butyl; T and U=O (double bond); V=methyl at the $\alpha$ position; W, Y and Z=H; X=OH.
Yield=27%
Melting point=146.5° C.
N.M.R.=1.00 (s, 18-$CH_3$); 1.12 (d, 6-$CH_3$)-1.47 (s, 19-$CH_3$); 2.02 (m, 11$\beta$-OH); 3.82 (s,21-$CH_2$); 6.02 (s, 4-CH)

EXAMPLE 8

9$\alpha$-fluoro-11$\beta$-hydroxy-16$\beta$-methyl-pregna-1,4-diene-3,20-dione (or betamethasone) 17-acetate, 21-thioacetate A=B=methyl; T and U=O (double bond); V and Y=H; X=$\beta$OH; Z=$\beta$-methyl.

500 ml of acetone and 8.83 grams (116 mmol) of S-thioacetic acid are placed in a reactor capable of withstanding low pressures.

25.8 ml of a 4.5 N methanolic solution of sodium methoxide (116 mmol) are added with stirring, over a period of 5 minutes, at ambient temperature.

After the mixture has been stirred at ambient temperature for 45 minutes, 49.5 grams (96.6 mmol) of betamethasone 17-acetate, 21-mesylate in solution in 900 ml of acetone are added.

The reactor is hermetically sealed and heated to 56° C.±2° C. for 5 hours. During this time, the contents of the reactor are stirred from time to time.

After cooling, about 700 ml of solvent are eliminated by distillation. The residue is precipitated in ice-cold water and the mixture is extracted with diethyl ether.

The 49 grams of residue obtained from this extraction with ether are purified by chromatography on a column containing 1.4 kg of "Florisil". This treatment by elution with a mixture of benzene and acetone yields 12.3 grams of product, which are subjected to a last purification by recrystallization from 140 ml of ethanol.

Weight=8.4 grams.
Yield=17.65%.
Melting point=207° C.
N.M.R.=0.95 (s, 18-$CH_3$); 1.32 (d, J=6 Hz, 16$\beta$-$CH_3$); 2.13 (s, methyl ester C-17); 2.40 (s, methyl thioester, 0.21); 3.13 (m, 11$\beta$ OH); 6.15 (s, 4-CH); 6.35 (d-d, J1=10 Hz J2=3 Hz, 2-CH); 7,30 (d, J=10 Hz, 1-CH).

The following products are prepared using the same procedure as in Example 8, with suitable reagents.

EXAMPLE 9

9α-fluoro-11β-hydroxy-16β-methyl-pregna-diene-3,20-dione (or betamethasone) 17-acetate, 21-thiopropionate.

A=ethyl; B=methyl; T and U=O (double bond); V and Y=H; X=βOH; Z=β-methyl.

Yield=13.3%

Melting point=193° C.

N.M.R.=0.93 (s, 18-$CH_3$); 1.17 (t, $CH_3$ ester 21); 1.35 (d, J=6 Hz, 16β-$CH_3$); 1.55 (s, 19-$CH_3$); 2.09 (s, methyl ester C-17); 2.20 (m, 11βON); 3.55 and 3.77 (d-d, J=7, 21-$CH_2$); 6.15 (s, 4-CH); 7.25 (d, J=10 Hz, 1-CH).

EXAMPLE 10

9α-fluoro-11β-hydroxy-16β-methyl-pregna-1,4-diene-3,20-dione (or betamethasone) 17-propionate, 21-thioacetate.

A=methyl; B=ethyl; T and U=O (double bond); V and Y=H; X=βOH; Z=β-methyl.

Yield=26.75%

Melting point=187.5° C.

N.M.R.=0.95 (s, 18-$CH_3$); 1.10 (t, methyl ester C-17); 1.36 (d, 16-CH); 2.32 (s, methyl ester 21); 3.40 (m, 11βOH); 3.68 (s, 21-$CH_2$); 7.35 (d, J=10 Hz 1-CH).

EXAMPLE 11

9α-fluoro-11β-hydroxy-16β-methyl-pregna-1,4-diene-3,20-dione (or betamethasone) 17-propionate, 21-thiopropionate.

A=B=ethyl; T and U=O (double bond); V and Y=H; X=βOH; Z=β-methyl.

Yield=31.2%.

Melting point=175° C.

N.M.R.=0.96 (s, 18-$CH_3$); 1.15 (t, $CH_3$ esters); 1.35 (d, 16β-CH); 1.55 (s, 19-$CH_3$); 2,80 (m, 11βOH); 3.50 and 3.82 (d, d, J=17 Hz, 21-$CH_2$).

EXAMPLE 12

9α-fluoro-11β-hydroxy-16β-methyl-pregna-1,4-diene-3,20-dione (or betamethasone) 17-valerate, 21-thiovalerate.

A=B=butyl; T and U=O (double bond); V and Y=H; X=βOH; Z=β-methyl

Yield=42.8%

Melting point=148° C.

N.M.R.=0.93 (t, $CH_3$ esters); 0.96 (s, 18-$CH_3$); 1.35 (d, J=6 Hz, 16β-$CH_3$); 1.55 (s, 19-$CH_3$); 2.18 (m, 11β-OH); 3.50–3.90 (d.d, J=17 Hz, 21-$CH_2$); 7.25 (d, J=10 Hz, 1-CH).

EXAMPLE 13

9α-fluoro-11β-hydroxy-16β-methyl-pregna-1,4-diene-3,20-dione (or betamethasone) 17-valerate, 21-thioacetate.

A=methyl; B=butyl; T and U=O (double bond); V and Y=H; X=βOH; Z=β-methyl.

Yield=37%

Melting point=127.5° C.

N.M.R.=0.97 (s, 18-$CH_3$); 1,32 (d, 16-$CH_3$β); 1.57 (s, 19-$CH_3$) 2.77 (m, 11-βOH); 6.15 (s, 4-CH)

EXAMPLE 14

9α-fluoro-11β-hydroxy-16α-methyl-pregna-1,4-diene-3,20-dione (or dexamethasone) 17-acetate, 21-thio-tert.butyl-acetate.

A=2,2-dimethyl-n-propyl; B=methyl; T and U=O (double bond); V and Y=H; W=α-fluoro; X=βOH; Z=α-methyl.

360 ml of HMPT and 18.5 grams (0.140 mol) of S-thio-tert.butylacetic acid are placed in a reactor.

At ambient temperature, 31.1 ml of a 4.5 N methanolic solution of sodium methoxide (0.140 mol) are added.

After one hour's stirring, 36.0 grams (0.070 mol) of dexamethasone 17-acetate, 21-mesylate in solution in 720 ml of HMPT are added over a period of about 15 minutes.

The reaction mixture is stirred for 24 hours at ambient temperature, precipitated in water and extracted with ether. The residue of the etheric phase is purified by 3 successive recrystalisations from a mixture of methanol and water (80:20 v/v).

Weight=15.5 grams

Yield=40.3%.

Melting point=149° C.

N.M.R.=0.91 (d, 16α-$CH_3$); 1.02 (s, 18-$CH_3$); 1.05 (s, t.butyl ester 21); 1.55 (s, 19-$CH_3$); 2.10 (s, $CH_3$ ester 17); 3.48 (s, 11β-OH); 7.25 (d, J=10 Hz, 1-CH).

EXAMPLE 15

9α-chloro-11β-hydroxy-16β-methyl-pregna-1,4-diene-3,20-dione (or beclomethasone) 17-propionate, 21-thiopropionate.

A=B=ethyl; T and U=O (double bond); V and Y=H; W=α-chloro; X=βOH; Z=β-methyl.

150 ml of acetone and 3.9 grams (43.2 mmol) of S-thiopropionic acid are placed in a reactor which can be hermetically sealed and which can withstand slight pressure.

Then 9.55 ml of a 4.5 N methanolic solution of sodium methoxide (43.2 mmol) are added. The mixture is stirred at ambient temperature for 45 minutes, then 13.0 grams (24 mmol) of beclomethasone 17-propionate, 21-mesylate in solution in 260 ml of acetone are added.

The mixture is stirred, then the hermetically sealed reactor is kept for 19 hours in a drying oven regulated to 60° C. In the course of time, the mixture becomes progressively darker, to end up black.

After cooling, the reaction medium is precipitated in 3 liters of cold water and extracted with ethyl ether.

The residue obtained from the etheric phases weighs 13.7 grams and takes the form of a greenish gum. It is purified by chromatography on a column of 430 grams of "Florisil".

By eluting with a mixture of methylene chloride and acetone (98:2 v/v) 7.5 grams of purified product are obtained which are subjected to a final recrystallisation from 60 ml of a mixture of methanol and water (80:20 v/v).

Weight=4.0 grams.

Yield=30%

Melting point=160° C.

N.M.R.=0.99 (s, 18-$CH_3$); 1.18 (t, $CH_3$ esters); 1.37 (d, 16β-$CH_3$; 1.68 (s, 19-$CH_3$); 1.80 (m, 11β-OH); 3.50, 3.85 (d.d, J=17 Hz, 21-$CH_2$); 7.25 (d, J=10 Hz, 1-CH.

The following compounds were prepared using the same procedure as in Example 15, with appropriate reagents:

EXAMPLE 16

9α-chloro-11β-hydroxy-16β-methyl-pregna-1,4-diene-3,20-dione (or beclomethasone) 17-propionate, 21-thiovalerate A=butyl; B=ethyl; T and U=O (double bond); V and Y=H; W=α-chloro; X=βOH; Z=β-methyl Yield=19%

Melting point=136° C.

N.M.R.=1.00 (s, 18-CH$_3$; 1.37 (d, 16-CH$_3$β); 1.70 (s, 19-CH$_3$); 2.38 (m, 11-βOH); 6.12 (s, 4-CH)

EXAMPLE 17

9α-chloro-11β-hydroxy-16β-methyl-pregna-1,4-diene-3,20-dione (or beclomethasone) 17-valerate, 21-thioacetate.

A=methyl; B==butyl; T and U=O (double bond); V and Y=H; W=α-chloro; X=βOH; Z=β-methyl Yield=55.8%

Melting point=138.5° C.

N.M.R.=1.00 (s, 18-CH$_3$); 1.37 (d, 16-βCH$_3$); 2.97 (m, 11-βOH); 6.12 (s, 4-CH)

EXAMPLE 18

9α-chloro-11β-hydroxy-16β-methyl-pregna-1,4-diene-3,20-dione (or beclomethasone) 17-valerate, 21-thiovalerate.

A and B=butyl; T and U=O (double bond); V and Y=H; W=α-chloro; X=βOH; Z=β-methyl Yield=35.4%

Melting point=210.5° C.

N.M.R.=0.98 (s, 18-CH$_3$); 1.38 (d, 16-βCH$_3$); 1.68 1.68 (s, 19-CH$_3$); 2.54 (m, 11-βOH); 6.10 (s, 4-CH).

EXAMPLE 19

11β-hydroxy-16-methylene-pregna-1,4-diene-3,20 dione (or prednylidene) 17-propionate, 21-thiopropionate A=B=ethyl; T and U=O (double bond); V, Y and W=H; X=βOH; Z=methylene. 123 mg (1.36 mmol) of S-thiopropionic acid and 4.5 ml of acetone are placed in a small reactor. 0.3 ml of a 4 N methanolic solution of sodium methoxide (1.36 mmol) are added.

The mixture is agitated for 1 hour at ambient temperature and then 460 mg (0.908 mmol) of prednylidene 17-propionate, 21-mesylate in solution in 12 ml of acetone are added.

The stirred mixture is heated to the reflux temperature of the acetone for 2 hours 15 minutes and then precipitated in water and extracted with ether.

The residue contained in the etheric phase weighs 450 mg; it is purified by chromatography on a column containing 21 grams of "Florisil".

By eluting with a mixture of dichloromethane and acetone (80:20 v/v) 200 mg of purified product are obtained, which is recrystallised from a mixture of methanol and water (80:20 v/v).

Weight=175 mg

Yield=98.5%

Melting point=164° C.

N.M.R.=1.05 (s, 18-CH$_3$)$_0$; 1.20 (t, CH$_3$ esters); 1.46 (s, 19-CH$_3$); 1.90 (m, 11β-OH); 3.95 (2, 21-CH$_2$); 5.55 (d, J=8 Hz, 16 methylene; 7.30 (d, J=10 Hz, 1-CH).

The compounds according to the invention, when administered to animals by routes which are compatible with their insolubility in water, do not show any acute toxicity.

The pharmacological activity of the products described in the invention was tested in the rat using a technique similar to that described by C. A. Winter and C. C. Porter (J. Am. Pharm. Ass. 1957, 46, 9, pages 515–519).

The principle of the test consists in implanting a pellet of cotton wool in the dorsal subcutaneous tissue of the animal. The corticoids to be studied are added to the pellet so that the following tests can be carried out:

(1) Determination of the local anti-inflammatory activity

The presence of products within the pellet may inhibit or prevent the formation of a granuloma.

(2) Determination of the systemic activity of the products after local administration Local application of the corticoids may result, inter alia, in:

(a) a reduction in the defence systems of the organism, the most notable sign of which is a reduction in the weight of the animals' thymuses.

(b) Disruption of the protein metabolism which causes tissue fusion, resulting in an inhibition of the weight increase in animals.

These effects were studied with the products of the invention, using the following procedure.

PROCEDURE

The animals are divided into random homogeneous groups of 10 male Sprague-Dawley I.O.P.S. rats with a body weight of between 100 and 120 grams.

The pellets to be implanted weigh from 35 to 40 mg and are prepared from balls of dental cotton wool. Before being inserted, each pellet is weighed and impregnated with the precise quantity of the product which is to be studied, dissolved in 0.2 ml of chloroform. The chloroform is eliminated by evaporation over a period of 24 hours at ambient temperature.

Before implantation, each pellet is impregnated with a solution of antibiotics:

Penicillin G 200,000 I.U./ml

Streptomycin 0.1 gram/ml.

The animals are anaesthetised with ether, and then two pellets are implanted in each animal in the dorsal subcutaneous tissue, on each side of the median line:

on the left, the pellet containing the product to be tested (treated animal) or the carrier only (control animal);

on the right, the pellet containing the carrier only.

The animals are given normal food and are sacrificed six days after the pellets have been implanted.

(1) Local anti-inflammatory activity

The pellets surrounded by granulomatous tissue are carefully removed and weighed, and then dried until a constant weight is obtained.

The activity of the products is expressed as the percentage inhibition compared with the values obtained with the control groups and more particularly the effective dose 50 of the product being studied (ED 50) which results in a 50% inhibition in weight.

(2) Determination of the systemic effect (a) Effect on the thymus

The thymuses are taken from the same animals and weighed. Using the same type of calculation, an ED 50 is determined, which corresponds to the dosage of product resulting in a 50% decrease in weight of the thymuses, compared with the control animals.

(b) Effect on weight gain

The weight gain over six days is determined on the animals before they are sacrificed.

The activity of the products was expressed as the percentage inhibition in the weight gain of the treated animals compared with the weight gain in the control animals.

The ED 30 which corresponds to a 30% inhibition in the weight gain was determined.

RESULTS (1) Local anti-inflammatory activity

The results are shown in Table 1. The relative activity of the test products compared with betamethasone 17,21-dipropionate is calculated according to the following equation:

$$R1 = \frac{ED\ 50\ DPB}{ED_{50}\ \text{test product}}$$

TABLE 1

| Product | $ED_{50}$ (mg/pellet) | R 1 |
|---|---|---|
| D.P.B. | 1.610 | 1 |
| Ex. 1 | <0.200 | >8 |
| Ex. 2 | 2.140 | 0.75 |
| Ex. 3 | 0.600 | 2.7 |
| Ex. 4 | 0.056 | 29 |
| Ex. 5 | 0.210 | 7.7 |
| Ex. 6 | 0.180 | 8.9 |
| Ex. 7 | 0.800 | 2.0 |
| Ex. 8 | 0.072 | 22 |
| Ex. 9 | 0.100 | 16 |
| Ex. 10 | 0.013 | 124 |
| Ex. 11 | 0.012 | 134 |
| Ex. 12 | <0.0125 | >129 |
| Ex. 13 | 0.050 | 32.2 |
| Ex. 14 | 0.003 | 537 |
| Ex. 15 | <0.005 | >322 |
| Ex. 16 | 0.120 | 13.4 |
| Ex. 17 | 0.180 | 8.9 |
| Ex. 18 | 0.096 | 16.8 |
| Ex. 19 | 1.800 | 0.89 |
| Beclomethasone dipropionate | >5 | <0.2 |

The majority of the products according to this invention show an activity which is equal to or greater than that of betamethasone 17,21-dipropionate in this test.

This is particularly remarkable for the products of Examples 10, 11, 12, 14 and 15 which have activities more than 100 times greater.

A comparison with beclomethasone 17,21-dipropionate is even more flattering for the compounds of the invention.

(2) Systemic effects after local application (a) Effects on the weight of the thymus In Table 2 which follows, the results obtained and a relative comparison with DPB (R2) are given:

TABLE 2

| PRODUCT | $ED_{50}$ (mg/pellet) | R 2 |
|---|---|---|
| D.P.B. | 0,86 | 1 |
| Ex. 1 | zero to 3.2 | <<0.27 |

TABLE 2-continued

| PRODUCT | $ED_{50}$ (mg/pellet) | R 2 |
|---|---|---|
| Ex. 2 | zero to 3.4 | <<0.25 |
| Ex. 3 | >>5 | <<0.17 |
| Ex. 4 | >>5 | <<0.17 |
| Ex. 5 | >>1 | <<0.86 |
| Ex. 6 | >>1 | <<0.86 |
| Ex. 7 | >>1 | <<0.86 |
| Ex. 8 | 1.20 | 0.71 |
| Ex. 9 | 1.70 | 0.51 |
| Ex. 10 | 0.25 | 3.40 |
| Ex. 11 | 0.46 | 1.9 |
| Ex. 12 | >>0.8 | <<1 |
| Ex. 13 | 0.8 | 1.1 |
| Ex. 14 | 0.33 | 2.6 |
| Ex. 15 | 2.4 | 0.36 |
| Ex. 16 | >>1 | <<0.86 |
| Ex. 17 | >>1 | <<0.86 |
| Ex. 18 | >>1 | <<0.86 |
| Ex. 19 | 7 | 0.12 |
| Beclomethasone dipropionate | 3.1 | 0.27 |

The effect on the weight of the thymus caused locally by the products of the invention compared with betamethasone 17,21-dipropionate is, for certain products, equal to or greater than this reference product.

It will be noted that some products (Examples 1-7, 16-19) have a significantly weaker effect.

(b) Effects on the weight gain

The results and relative activity R3, calculated in the same way as before, starting from the ED30, are shown in Table 3.

TABLE 3

| PRODUCT | $ED_{30}$ (mg/pellet) | R 3 |
|---|---|---|
| D.P.B. | >>0.8 | 1 |
| Ex. 1 | >>3.2 | <<0.25 |
| Ex. 2 | >>3.4 | <<0.24 |
| Ex. 3 | >5 | <0.16 |
| Ex. 4 | >5 | <0.16 |
| Ex. 5 | >>1 | <<0.8 |
| Ex. 6 | >>1 | <<0.8 |
| Ex. 7 | >>1 | <<0.8 |
| Ex. 8 | 1 | 0.8 |
| Ex. 9 | 1 | 0.8 |
| Ex. 10 | >1 | <0.8 |
| Ex. 11 | 0.8 | 1 |
| Ex. 12 | >>0.8 | <<1 |
| Ex. 13 | 0.65 | 1.23 |
| Ex. 14 | 0.015 | 53 |
| Ex. 15 | 0.56 | 1.42 |
| Ex. 16 | >>1.0 | <<0.8 |
| Ex. 17 | >>1.0 | <<0.8 |
| Ex. 18 | >>1.0 | <<0.8 |
| Ex. 19 | 0.015 | 53 |
| Beclomethasone dipropionate | 5 | 0.16 |

The majority of the products of the invention have an activity which is comparable with or inferior to that of betamethasone 17,21-dipropionate, used as a reference substance.

To sum up, from the pharmacological tests carried out, the products of the invention have a useful local anti-inflammatory activity which is equal to and in some cases far superior to than that of betamethasone 17,21-dipropionate, used as a reference substance.

Moreover, the results of the tests carried out to investigate the systemic effects show that the majority of the products of the invention have an activity inferior to that of the reference substance.

The superiority of the products according to the invention over the reference substance may be expressed by the ratio R1/R2 which, in the case of R1, takes account of the local anti-inflammatory activity and, in R2, takes account of the systemic activity.

$$R4 = \frac{R1}{R2} = \frac{ED_{50} \text{ D.P.B. (pellet)}}{ED_{50} \text{ products (pellet)}} \times \frac{ED_{50} \text{ products (thymus)}}{ED_{50} \text{ D.P.B. (thymus)}}$$

Consequently, the higher the value of R4, the more favourable the local anti-inflammatory activity of the product of the Example, compared with betamethasone 17,21-dipropionate (D.P.B.). The results of these calculations are given in Table 4.

TABLE 4

| Product | R 4 |
|---|---|
| D.P.B. | 1 |
| Ex. 1 | 30 |
| Ex. 2 | 3 |
| Ex. 3 | 16 |
| Ex. 4 | 171 |
| Ex. 5 | >9 |
| Ex. 6 | >10 |
| Ex. 7 | >2 |
| Ex. 8 | 31 |
| Ex. 9 | 31 |
| Ex. 10 | 36 |
| Ex. 11 | 71 |
| Ex. 12 | 129 |
| Ex. 13 | 29 |
| Ex. 14 | 207 |
| Ex. 15 | 894 |
| Ex. 16 | >16 |
| Ex. 17 | >16 |
| Ex. 18 | >20 |
| Ex. 19 | 7 |
| Beclomethasone dipropionate | 0.7 |

These results demonstrate the valuable local anti-inflammatory properties of the compounds according to the invention.

The compounds of Examples 4, 11, 12, 14 and 15 are particularly preferred.

The products of the invention may be administered in man by the routes which are appropriate for the different sites of the inflammatory complaints, in the form of pharmaceutical compositions adapted for administration by topical and/or systemic route.

The quantity of active steroid in these pharmaceutical compositions depends on the intrinsic anti-inflammatory activity of this steroid and the nature of the inflammatory complaint which is to be treated.

Compositions administered by topical route may advantageously contain the active ingredient in quantities of between 0.01 and 5% by weight in admixture with a conventional excipient. These compositions may be administered one to several times a day depending on the nature and gravity of the complaint being treated.

For systemic administration, the compositions used may contain from 0.1 to 100 mg of active product per dosage unit of from 0.1 to 100 grams, depending on the nature of the active agent. The quantity of active substance administered daily may vary from 0.1 to 300 mg.

It will be understood that the pharmaceutical compositions may contain other active substances. These may be, for example, substances such as preservatives, bacteriostatic agents, antibiotics, antimycotic agents and local anaesthetics.

For topical application the active substances are incorporated in excipients or carriers conventionally used for the preparation of pharmaceutical compositions suitable for this form of administration. These compositions may be, for example, ointments, lotions, creams, emulsions, drops, enemas, suppositories, ovules, instillations or aerosols.

The pharmaceutical compositions adapted for systemic administration may be in liquid or solid form; they are used in the conventional manner in human medicine. These compositions may be, for example, solutions and suspensions, which may or may not be injectable, and tablets, capsules, granules and gelatine capsules for the solid forms.

The Examples which follow provide a non-restrictive illustration of the formulations and methods of production of some pharmaceutical compositions suitable for the administration of the products according to the invention.

| Tablets | Quantities per 100 g |
|---|---|
| Product of Example 1 | 0.50 g |
| Microcrystalline cellulose | 93.50 g |
| Polyvinylpyrrolidone | 1.00 g |
| Carboxymethyl starch | 4.00 g |
| Magnesium stearate | 1.00 g |

Method of Production

In a suitable mixer, the microcrystalline cellulose and some of the carboxymethyl starch are moistened with an alcoholic solution of polyvinylpyrrolidone in which the active substance has been dissolved.

The granulate obtained is then dried, screened and mixed with magnesium stearate and the remaining carboxymethyl starch, and finally compressed in a rotary tablet-making machine.

| Ointment | Quantity per 100 g |
|---|---|
| Product of Example 8, micronised | 0.050 g |
| Vaseline | 40.000 g |
| Vaseline oil | 15.000 g |
| White wax | 4.000 g |
| Sorbitan sesquioleate | 6.000 g |
| Purified water q.s.ad | 100.000 g |

Method of Production

The aqueous phase heated to 75° C. is incorporated, with stirring, in the fatty phase which has previously been heated to 70° C.

The micronised active substance is incorporated in the ointment.

After homogenisation the ointment is packed into tubes.

| Cream | Quantity per 100 g |
|---|---|
| Product of Example 7, micronised | 0.050 g |
| Cetylstearyl alcohol | 8.000 g |
| Vaseline oil | 10.000 g |
| Isopropyl myristate | 5.000 g |
| Propylene glycol | 5.000 g |
| Sorbitan monostearate POE | 2.50 g |
| Sorbiton monostearate | 1.50 g |
| Sorbic acid | 0.200 g |
| Sodium hydroxide q.s.pH. | 5.5 |

| Cream | Quantity per 100 g |
|---|---|
| —continued | |
| Purified water q.s.ad | 100.000 g |

Method of Production

The sorbic acid is dissolved in the fatty phase which has previously been heated to 70° C.

The aqueous phase, heated to 75° C. and containing the emulsifiers, is added to the gaseous phase.

The micronised active substance is incorporated in the emulsion thus formed.

After homogenisation, the cream is packed into tubes.

| Enema | Quantity per 100 ml |
|---|---|
| Product of Example 9 | 0.005 g |
| Polysorbate 80 | 0.050 g |
| Monosodium phosphate | 0.150 g |
| Sodium chloride | 0.700 g |
| Low viscosity sodium carboxymethyl cellulose | 0.500 g |
| Benzyl alcohol | 0.900 g |
| Sodium hydroxide q.s.ad pH | 6.8 |
| Purified water q.s.ad | 100.00 ml. |

Method of production

The polysorbate 80, monosodium phosphate and sodium chloride are dissolved in the purified water. Then the sodium carboxymethyl cellulose and the micronised active product are dispersed in this solution.

The pH of the suspension is adjusted to 6.8 with a sodium hydroxide solution.

After homogenisation, the suspension is transferred into vials each containing 100 ml.

| Suspension for use in nose and ears | Quantity per 100 ml |
|---|---|
| Product of Example 2, micronised | 1.000 g |
| N—cetylpyridinium chloride | 0.020 g |
| Monosodium phosphate | 0.150 g |
| Sodium chloride | 0.750 g |
| Sodium hydroxide q.s.ad pH | 6.8 |
| Benzyl alcohol | 0.900 g |
| Purified water q.s.ad | 100.000 ml |

Method of production

The N-cetylpyridinium chloride, monosodium phosphate, sodium chloride and benzyl alcohol are dissolved in the purified water, with stirring.

The micronised active substance is dispersed in this solution. The pH of the suspension is then adjusted to pH 6.8 with sodium hydroxide solution.

After homogenisation, the suspension is transferred into vials each containing 10 ml.

| Aerosol | Quantity for a 10 ml vial |
|---|---|
| Product of Example 1, micronised | 10 mg |
| Sorbitan trioleate | 50 mg |
| Trichlorofluoromethane (F11) | 10 mg |
| Dichlorodifluoromethane (F12) q.s.ad | |
| Dichlorotetrafluoroethane (F114) | |

Method of Production

The active substance is suspended in some of the trichloromethane (F11) in which the sorbitan trioleate has previously been dispersed.

The suspension obtained is transferred into aerosol containers which are then fitted with a metering valve.

The remaining trichlorofluoromethane and the dichlorodifluoromethane and dichlorotetrafluoroethane are then injected.

| Injectable Suspension | Quantity per 100 ml |
|---|---|
| Product of Example 4, micronised | 2.000 g |
| Polysorbate 80 | 0.050 g |
| Sodium chloride | 0.780 g |
| Low viscosity sodium carboxymethyl cellulose | 0.500 g |
| Benzyl alcohol | 0.900 g |
| Water for injectable preparation q.s.ad | 100.000 ml |

Method of Production

The polysorbate 80, sodium chloride and benzyl alcohol are dissolved in some of the water for injection.

The solution is then sterilised and the micronised active substance, which has itself already been sterilised, is dispersed in this solution.

A sterile solution of sodium carboxymethyl cellulose is added to the suspension.

After homogenisation, the suspension is transferred into ampoules, in quantities of 5 ml per ampoule.

| Lotion | Quantity per 100 ml |
|---|---|
| Product of Example 7, micronised | 0.100 g |
| Glycerine | 7.500 |
| Isopropyl alcohol | 15.000 |
| Carboxypolymethylene | 0.150 |
| Sodium hydroxide q.s.ad pH | 7 |
| Purified water q.s.ad | 100.000 ml |

Method of production

The active principle is dispersed in the aqueous alcoholic phase which is then gelatinised slightly by the addition of carboxypolymethylene and sodium hydroxide.

THERAPEUTIC INDICATIONS

The products of the invention have a powerful anti-inflammatory activity and have only slight glucocorticoid effects.

The pharmaceutical compositions containing these products are particularly useful for treating inflammatory, pruriginous and allergic complaints.

On the skin and mucous membranes, they are used for the treatment of rectal complaints and complaints of the colon, eczema and dermatitis of various etiologies, lichenification and psoriasis. Similarly, their action on the mucous membranes of the O.R.L. region and bronchi is particularly valuable, especially in the treatment of asthma.

These compositions are also valuable for treating internal complaints such as arthritis and polyarthritis and for various diseases of allergic origin.

What is claimed is:

1. A compound of formula:

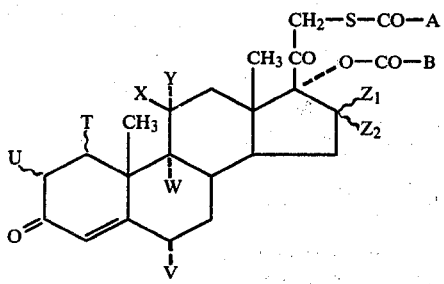

wherein A represents a straight-chained or branched alkyl group having from 1 to 6 carbon atoms and B represents a straight-chained or branched alkyl group having from 1 to 6 carbon atoms or a phenyl group, T and U, independently of each other, represent hydrogen atoms or together form a double bond, V is a hydrogen atom or a methyl group at the α-position, W is a hydrogen atom, a fluorine or a chlorine atom at the α-position, X is a hydroxy group at the β-position and Y is a hydrogen atom or X and Y may together represent an oxygen atom, and $Z_1$ is a hydrogen atom, a methyl group at the α- or β-position, $Z_2$ is a hydrogen atom, or $Z_1$ and $Z_2$ together form a methylen group.

2. The compound of claim 1 which is 9α-Fluoro-11β-hydroxy-16β-methyl-pregna-1,4-diene-3,20-dione 17-propionate, 21-thiopropionate.

3. The compound of claim 1 which is 9α-Fluoro-11β-hydroxy-16β-methyl-pregna-1,4-diene-3,20-dione 17-valerate 21-thiovalerate.

4. The compound of claim 1 which is 9α-Fluoro-11β-hydroxy-16α-methyl-pregna-1,4-diene-3,20-dione 17-acetate, 21-thiotert.butylate.

5. The compound of claim 1 which is 9α-Chloro-11β-hydroxy-16β-methyl-pregna-1,4-diene-3,20-dione 17-propionate, 21-thiopropionate.

6. The compound of claim 1 which is 11β-Hydroxy-pregn-4-ene-3,20-dione 17-valerate, 21-thiovalerate.

7. The compound of claim 1 which is Pregna-1,4-diene-3,11,20-trione 17-butyrate, 21-thioacetate.

8. The compound of claim 1 which is 11β-Hydroxy-6α-methyl-pregna-1,4-diene-3,20-dione 17-benzoate, 21-thioacetate.

9. The compound of claim 1 which is 11β-Hydroxy-6α-methyl-pregna-1,4-diene-3,20-dione 17propionate, 21-thiopropionate.

10. The compound of claim 1 which is 11β-Hydroxy-6α-methyl-pregna-1,4-diene-3,20-dione 17-valerate, 21-thioacetate.

11. The compound of claim 1 which is 9α-Fluoro-11β-hydroxy-16β-methyl-pregna-1,4-diene-3,20-dione 17-acetate, 21-thioacetate.

12. The compound of claim 1 which is 9α-Fluoro-11β-hydroxy-16β-methyl-pregna-1,4-diene-3,20-dione 17-acetate, 21-thiopropionate.

13. The compound of claim 1 which is 9α-Fluoro-11β-hydroxy-16β-methyl-pregna-1,4-diene-3,20-dione 17-propionate, 21-thioacetate.

14. The compound of claim 1 which is 11β-Hydroxy-16-methylene-pregna-1,4-diene-3,20-dione 21-thiopropionate.

15. The compound of claim 1 which is 9α-Fluoro-11β-hydroxy-16β-methyl-pregna-1,4-diene-3,20-dione 17-valerate, 21-thioacetate.

16. The compound of claim 1 which is 9α-Chloro-11β-hydroxy-16β-methyl-pregna-1,4-diene-3,20-dione 17-propionate, 21-thiovalerate.

17. The compound of claim 1 which is 9α-Chloro-11β-hydroxy-16β-methyl-pregna-1,4-diene-3,20-dione 17-valerate, 21-thioacetate.

18. The compound of claim 1 which is 9α-Chloro-11β-hydroxy-16β-methyl-pregna-1,4-diene-3,20-dione 17-valerate, 21-thiovalerate.

19. An anti-inflammatory, anti-pruriginous, anti-allergic and anti-asthmatic medicament, which comprises an active amount of a compound of formula:

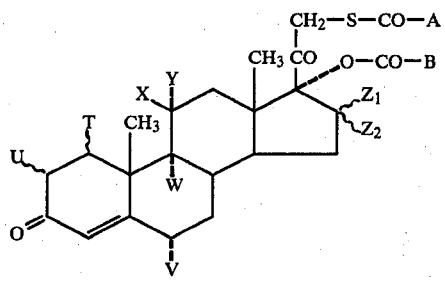

wherein A and B each represent, independently of each other, a straight-chained or branched alkyl group having from 1 to 6 carbon atoms or a phenyl group optionally mono- or polysubstituted by alkyl radicals having from 1 to 6 carbon atoms, alkoxy groups having form 1 to 6 carbon atoms or halogen, T and U, independently of each other, represent hydrogen atoms or together form a double bond, V is a hydrogen atom or a methyl group at the α-position, W is a hydrogen atom or a halogen atom at the α-position, X is a hydroxy group at the β-position and Y is a hydrogen atom or X and Y may together represent an oxygen atom, and $Z_1$ is a hydrogen atom, a methyl group at the α- or β-position, whilst $Z_2$ is a hydrogen atom, or $Z_1$ and $Z_2$ together form a methylene group in admixture with pharmaceutically acceptable vehicle.

20. A compound of formula:

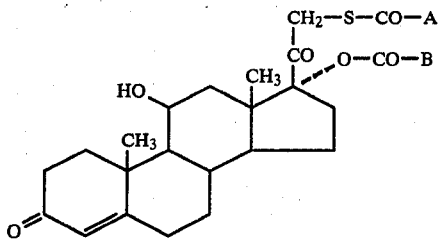

wherein a is a straight-chained or branched alkyl group having from 1 to 6 carbon atoms and B represents a straight-chained or branched alkyl group having from 1 to 6 carbon atoms or a phenyl group.

21. The compound of claim 20 which is 11β-hydroxy-pregn-4-ene-3, 20-dione-17-valerate, 21-thiovalerate.

22. The compound of claim 20 which is 11β-hydroxy-pregn-4-ene-3, 20-dione-17-valerate, 21-thiopivalate.

23. A process for preparing the compound of claim 22 comprising reacting a 21-sulphonate of the formula

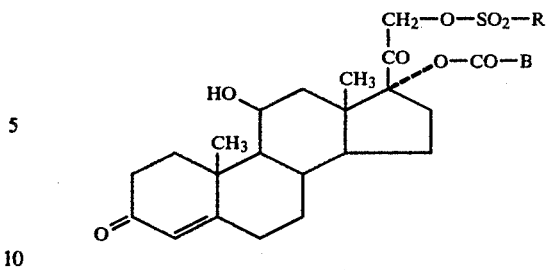
wherein R is lower alkyl with an alkali metal thiocarboxylate of the formula, M—S—CO—A, wherein M is an alkali metal atom and A and B have the meanings given in claim 20.
24. An anti-inflammatory, anti-pruriginous, anti-allergic and anti-asthmatic medicament comprising an active amount of the compound of claim 20 in admixture with a pharmaceutically acceptable vehicle.
* * * * *